(12) United States Patent
Lee et al.

(10) Patent No.: US 7,691,390 B2
(45) Date of Patent: Apr. 6, 2010

(54) VIRAL PROTEIN

(76) Inventors: Fang-Jen Lee, 1F, No. 326, Sec. 2, Shih-Pol Road, Taipei (TW); Chia-Jung Yu, 811 Room, 7 Chang Gung Village, Kwei-San, Tao-Yuan (TW); Ming-Fu Chang, 6F, No. 15-1, Alley 97, Sec. 1, Shin-Sen South Road, Taipei (TW); Hong-Nerng Ho, 9F, No. 23-1, Sec. 3, Shin-Sen South Road, Taipei (TW)

( * ) Notice: Subject to any disclaimer, the term of this patent is extended or adjusted under 35 U.S.C. 154(b) by 115 days.

(21) Appl. No.: 11/857,961

(22) Filed: Sep. 19, 2007

(65) Prior Publication Data

US 2009/0068636 A1 Mar. 12, 2009

Related U.S. Application Data

(62) Division of application No. 11/071,569, filed on Mar. 2, 2005, now abandoned.

(60) Provisional application No. 60/549,277, filed on Mar. 2, 2004.

(51) Int. Cl.
   *A61K 39/215* (2006.01)
   *A61K 39/00* (2006.01)
   *A61K 38/00* (2006.01)
   *A61K 39/38* (2006.01)
   *A61K 39/12* (2006.01)
(52) U.S. Cl. .............. 424/221.1; 424/184.1; 424/185.1; 424/186.1; 530/300
(58) Field of Classification Search ................ None
   See application file for complete search history.

(56) References Cited

U.S. PATENT DOCUMENTS 7,220,852 B1 * 5/2007 Rota et al. ............... 536/23.72

OTHER PUBLICATIONS

"SARS Coronavirus Tor2, Complete Genome", Database EMBL-EBI AY274119.3, Apr. 15, 2003.
"Human Coronavirus (Strain SARS)", Database Uniprot P59632, Jan. 10, 2003.
"Isolation and Characterization of Viruses Related to the SARS Coronavirus from Animals in Southern China", EMBL-SVA AU304494.1, Nov. 6, 2003.
Marra, et al. "The Genome Sequence of the SARS-Associated Coronavirus", Science 300:1399-1404, May 30, 2003.
Rota, et al., "Characterization of a Novel Coronavirus Associated with Severe Acute Respiratory Syndrome", Science 300:1394-1399, May 30, 2003.
De Groot, "How the SARS Vaccine Effort can Learn from HIV—Speeding Towards the Future, Learning from the Past", Vaccine 21:4095-4104, Oct. 1, 2003.
Ping, et al., "DNA Vaccine of SARS-Cov S Gene Induces Antibody Response in Mice", US National Library of Medicine, Accession No. NLM14732873, Jan. 2004.
Snijder, et al., "Unique and Conserved Features of Genome and Proteome of SARS-Coronavirus, an Early Split-off from the Coronavirus Group 2 Lineage", Journal of Molecular Biology, Aug. 2003, vol. 331, p. 991-1004.
Rota, et al., GenBank Accession No. P59632 [online]. National Center for Biotechnology Information, Apr. 23, 2003 [retrieved on Jun. 6, 2007]. Retrieved from the Internet <URL: www.ncbi.nlm.nih.gov/entrez/viewer.fcgi?db=protein&id=30173393>.
Tan, Yee-Joo, "The Severe Acute Respiratory Syndrome (SARS)-Coronavirus 3a Protein may Function as a Modular of the Trafficking Properties of the Spike Protein", Virology Journal, 2005, vol. 2:5, Feb. 10, 2005.
Yu, et al.,"Identification of a Novel Protein 3a from Severe Acute Respiratory Syndrome Coronavirus", FEBS Lett., May 7, 2004, vol. 565(1-3), p. 111-6. Abstract and Uncorrected Proof.
"SARS Coronavirus TW1, Complete Genome", Database NCBI AY291451, Feb. 25, 2004.
"SARS Coronavirus Urbani, Complete Genome", Database NCBI AY278741, Apr. 21, 2003.

* cited by examiner

*Primary Examiner*—Jeffrey S Parkin
*Assistant Examiner*—Louise Humphrey
(74) *Attorney, Agent, or Firm*—Howrey LLP; Viola T. Kung

(57) ABSTRACT

The present invention is directed to an isolated polypeptide containing SEQ ID NO: 1 or an immunogenic fragment thereof. Also disclosed is an isolated nucleic acid encoding the polypeptide or containing a sequence at least 70% identical to SEQ ID NO: 3. Within the scope of this invention are related expression vectors, host cells, and antibodies. Also disclosed are methods of producing the polypeptide, diagnosing coronavirus infection, and identifying a test compound for treating coronavirus infection.

8 Claims, No Drawings

SEQUENCE LISTING

<160> NUMBER OF SEQ ID NOS: 12

<210> SEQ ID NO 1
<211> LENGTH: 274
<212> TYPE: PRT
<213> ORGANISM: SARS coronavirus

<400> SEQUENCE: 1

| | | | | | | | | | | | | | | |
|---|---|---|---|---|---|---|---|---|---|---|---|---|---|---|
|Met|Asp|Leu|Phe|Met|Arg|Phe|Phe|Thr|Leu|Gly|Ser|Ile|Thr|Ala|Gln|
|1| | | |5| | | | |10| | | | |15|
|Pro|Val|Lys|Ile|Asp|Asn|Ala|Ser|Pro|Ala|Ser|Thr|Val|His|Ala|Thr|
| | | |20| | | | |25| | | | |30| | |
|Ala|Thr|Ile|Pro|Leu|Gln|Ala|Ser|Leu|Pro|Phe|Gly|Trp|Leu|Val|Ile|
| | |35| | | | |40| | | | |45| | | |
|Gly|Val|Ala|Phe|Leu|Ala|Val|Phe|Gln|Ser|Ala|Thr|Lys|Ile|Ile|Ala|
| |50| | | | |55| | | | |60| | | | |
|Leu|Asn|Lys|Arg|Trp|Gln|Leu|Ala|Leu|Tyr|Lys|Gly|Phe|Gln|Phe|Ile|
|65| | | | |70| | | | |75| | | | |80|
|Cys|Asn|Leu|Leu|Leu|Leu|Phe|Val|Thr|Ile|Tyr|Ser|His|Leu|Leu|Leu|
| | | | |85| | | | |90| | | | |95| |
|Val|Ala|Ala|Gly|Met|Glu|Ala|Gln|Phe|Leu|Tyr|Leu|Tyr|Ala|Leu|Ile|
| | | |100| | | | |105| | | | |110| | |
|Tyr|Phe|Leu|Gln|Cys|Ile|Asn|Ala|Cys|Arg|Ile|Ile|Met|Arg|Cys|Trp|
| | |115| | | | |120| | | | |125| | | |
|Leu|Cys|Trp|Lys|Cys|Lys|Ser|Lys|Asn|Pro|Leu|Leu|Tyr|Asp|Ala|Asn|
| |130| | | | |135| | | | |140| | | | |
|Tyr|Phe|Val|Cys|Trp|His|Thr|His|Asn|Tyr|Asp|Tyr|Cys|Ile|Pro|Tyr|
|145| | | | |150| | | | |155| | | | |160|
|Asn|Ser|Val|Thr|Asp|Thr|Ile|Val|Val|Thr|Glu|Gly|Asp|Gly|Ile|Ser|
| | | | |165| | | | |170| | | | |175| |
|Thr|Pro|Lys|Leu|Lys|Glu|Asp|Tyr|Gln|Ile|Gly|Gly|Tyr|Ser|Glu|Asp|
| | | |180| | | | |185| | | | |190| | |
|Arg|His|Ser|Gly|Val|Lys|Asp|Tyr|Val|Val|His|Gly|Tyr|Phe|Thr|
| | |195| | | | |200| | | | |205| | | |
|Glu|Val|Tyr|Tyr|Gln|Leu|Glu|Ser|Thr|Gln|Ile|Thr|Thr|Asp|Thr|Gly|
| | |210| | | | |215| | | | |220| | | |
|Ile|Glu|Asn|Ala|Thr|Phe|Phe|Ile|Phe|Asn|Lys|Leu|Val|Lys|Asp|Pro|
|225| | | | |230| | | | |235| | | | |240|
|Pro|Asn|Val|Gln|Ile|His|Thr|Ile|Asp|Gly|Ser|Ser|Gly|Val|Ala|Asn|
| | | | |245| | | | |250| | | | |255| |
|Pro|Ala|Met|Asp|Pro|Ile|Tyr|Asp|Glu|Pro|Thr|Thr|Thr|Thr|Ser|Val|
| | | |260| | | | |265| | | | |270| | |
|Pro|Leu| | | | | | | | | | | | | | |

<210> SEQ ID NO 2
<211> LENGTH: 15
<212> TYPE: PRT
<213> ORGANISM: SARS coronavirus

<400> SEQUENCE: 2

Asp Pro Ile Tyr Asp Glu Pro Thr Thr Thr Thr Ser Val Pro Leu
1               5                   10                  15

<210> SEQ ID NO 3
<211> LENGTH: 825
<212> TYPE: DNA
<213> ORGANISM: SARS coronavirus

<400> SEQUENCE: 3
atggatttgt ttatgagatt ttttactctt ggatcaatta ctgcacagcc agtaaaaatt 60
gacaatgctt ctcctgcaag tactgttcat gctacagcaa cgataccgct acaagcctca 120

```
ctcccttcg  gatggcttgt  tattggcgtt  gcatttcttg  ctgttttca  gagcgctacc      180 aaaataattg  cgctcaataa  aagatggcag  ctagcccttt  ataagggctt  ccagttcatt      240
tgcaatttac  tgctgctatt  tgttaccatc  tattcacatc  ttttgcttgt  cgctgcaggt      300
atggaggcgc  aatttttgta  cctctatgcc  ttgatatatt  ttctacaatg  catcaacgca      360
tgtagaatta  ttatgagatg  ttggctttgt  tggaagtgca  aatccaagaa  cccattactt      420
tatgatgcca  actactttgt  ttgctggcac  acacataact  atgactactg  tataccatat      480
aacagtgtca  cagatacaat  tgtcgttact  gaaggtgacg  gcatttcaac  accaaaactc      540
aaagaagact  accaaattgg  tggttattct  gaggataggc  actcaggtgt  taaagactat      600
gtcgttgtac  atggctattt  caccgaagtt  tactaccagc  ttgagtctac  acaaattact      660
acagacactg  gtattgaaaa  tgctacattc  ttcatcttta  caagcttgt  taaagaccca      720 ccgaatgtgc  aaatacacac  aatcgacggc  tcttcaggag  ttgctaatcc  agcaatggat      780
ccaatttatg  atgagccgac  gacgactact  agcgtgcctt  gtaa                        825

<210> SEQ ID NO 4
<211> LENGTH: 45
<212> TYPE: DNA
<213> ORGANISM: SARS coronavirus

<400> SEQUENCE: 4
gatccaattt  atgatgagcc  gacgacgact  actagcgtgc  ctttg                       45

<210> SEQ ID NO 5
<211> LENGTH: 14
<212> TYPE: PRT
<213> ORGANISM: SARS coronavirus

<400> SEQUENCE: 5

Pro Ile Tyr Asp Glu Pro Thr Thr Thr Thr Ser Val Pro Leu
1               5                   10

<210> SEQ ID NO 6
<211> LENGTH: 42
<212> TYPE: DNA
<213> ORGANISM: SARS coronavirus

<400> SEQUENCE: 6
ccaatttatg  atgagccgac  gacgactact  agcgtgcctt  tg                          42

<210> SEQ ID NO 7
<211> LENGTH: 15
<212> TYPE: PRT
<213> ORGANISM: Artificial Sequence
<220> FEATURE:
<223> OTHER INFORMATION: Synthetically generated peptide

<400> SEQUENCE: 7

Cys Pro Ile Tyr Asp Glu Pro Thr Thr Thr Thr Ser Val Pro Leu
1               5                   10                  15

<210> SEQ ID NO 8
<211> LENGTH: 13
<212> TYPE: PRT
<213> ORGANISM: Artificial Sequence
<220> FEATURE:
<223> OTHER INFORMATION: Synthetically generated peptide
```

```
-continued

<400> SEQUENCE: 8

Ser Asp Asn Gly Pro Gln Ser Asn Gln Arg Ser Ala Cys
1               5                   10

<210> SEQ ID NO 9
<211> LENGTH: 27
<212> TYPE: DNA
<213> ORGANISM: Artificial Sequence
<220> FEATURE:
<223> OTHER INFORMATION: Primer

<400> SEQUENCE: 9
atggatttgt ttatgagatt ttttact                                          27

<210> SEQ ID NO 10
<211> LENGTH: 24
<212> TYPE: DNA
<213> ORGANISM: Artificial Sequence
<220> FEATURE:
<223> OTHER INFORMATION: Primer

<400> SEQUENCE: 10
caaaggcacg ctagtagtcg tcgt                                             24

<210> SEQ ID NO 11
<211> LENGTH: 9
<212> TYPE: PRT
<213> ORGANISM: SARS coronavirus

<400> SEQUENCE: 11

Met Asp Leu Phe Met Arg Phe Phe Thr
1               5

<210> SEQ ID NO 12
<211> LENGTH: 8
<212> TYPE: PRT
<213> ORGANISM: SARS coronavirus

<400> SEQUENCE: 12

Thr Thr Thr Thr Ser Val Pro Leu
1               5
```

VIRAL PROTEIN

This application is a divisional of U.S. application Ser. No. 11/071,569, filed Mar. 2, 2005 now abandoned; which claims priority to U.S. Provisional Application No. 60/549,277, filed Mar. 2, 2004; the contents of which are incorporated by reference in their entirety.

BACKGROUND

Virus is the cause of various infectious disorders. For example, members of the coronavirus family cause hepatitis in mice, gastroenteritis in pigs, and respiratory infections in birds and humans. Among the more than 30 coronaviruses isolated so far, three or four infect humans. The severe acute respiratory syndrome (SARS), a newly found infectious disease, is associated with a novel coronavirus. This life-threatening respiratory coronavirus touched off worldwide outbreaks in 2003. Vaccines and drugs against SARS coronavirus are being vigorously sought. Nevertheless, the progress is rather slow due to safety concerns.

SUMMARY

This invention is based, at least in part, on the discovery of SARS CoV protein 3a, which can serve as a target for elucidating the mechanisms of SARS and developing vaccines and therapeutics.

Listed below are the nucleic acid and amino acid sequences of this protein:

```
SEQ ID NO: 1
M D L F M R F F T L G S I T A Q P V K I

D N A S P A S T V H A T A T I P L Q A S

L P F G W L V I G V A F L A V F Q S A T

K I I A L N K R W Q L A L Y K G F Q F I

C N L L L L F V T I Y S H L L L V A A G

M E A Q F L Y L Y A L I Y F L Q C I N A

C R I I M R C W L C W K C K S K N P L L

Y D A N Y F V C W H T H N Y D Y C I P Y

N S V T D T I V V T E G D G I S T P K L

K E D Y Q I G G Y S E D R H S G V K D Y

V V V H G Y F T E V Y Y Q L E S T Q I T

T D T G I E N A T F F I F N K L V K D P

P N V Q I H T I D G S S G V A N P A M D

P I Y D E P T T T T S V P L

SEQ ID NO: 3
atggatttgtttatgagattttttactcttggatcaattactgcacagccagtaaaaatt gacaatgcttctcctgcaagtactgttcatgctacagcaacgataccgctacaagcctca ctcccttcggatggcttgttattggcgttgcatttcttgctgtttttcagagcgctacc aaaataattgcgctcaataaaagatggcagctagcccttttataagggcttccagttcatt tgcaatttactgctgctatttgttaccatctattcacatcttttgcttgtcgctgcaggt atggaggcgcaattttttgtacctctatgccttgatatattttctacaatgcatcaacgca tgtagaattattatgagatgttggctttgttggaagtgcaaatccaagaacccattactt tatgatgccaactactttgtttgctggcacacacataactatgactactgtataccatat aacagtgtcacagatacaattgtcgttactgaaggtgacggcatttcaacaccaaaactc aaagaagactaccaaattggtggttattctgaggataggcactcaggtgttaaagactat gtcgttgtacatggctatttcaccgaagtttactaccagcttgagtctacacaaattact acagacactggtattgaaaatgctacattcttcatcttttaacaagcttgttaaagaccca ccgaatgtgcaaatacacacaatcgacggctcttcaggagttgctaatccagcaatggat ccaatttatgatgagccgacgacgactactagcgtgcctttgtaa
```

One aspect of the invention features an isolated polypeptide containing SEQ ID NO: 1 or an immunogenic fragment derived from SEQ ID NO: 1. The immunogenic fragment is at least 10 amino acid residues in length, i.e., any number between 10 and 274 (the length of SEQ ID NO: 1), inclusive. Examples of such an immunogenic fragment include DPIY-DEPTTTTSVPL (SEQ ID NO: 2) and PIYDEPTTTTSVPL (SEQ ID NO: 5). The polypeptide can be used to generate antibodies that bind to protein 3a. An isolated polypeptide refers to a polypeptide substantially free from naturally associated molecules, i.e., it is at least 75% (i.e., any number between 75% and 100%, inclusive) pure by dry weight. Purity can be measured by any appropriate standard method, for example, by column chromatography, polyacrylamide gel electrophoresis, or HPLC analysis. An isolated polypeptide of the invention can be purified from a natural source, produced by recombinant DNA techniques, or by chemical methods.

Another aspect of the invention features an isolated nucleic acid containing a sequence encoding SEQ ID NO: 2 (e.g., gat cca att tat gat gag ccg acg acg act act agc gtg cct ttg; i.e., SEQ ID NO: 4), SEQ ID NO: 5 (e.g., cca att tat gat gag ccg acg acg act act agc gtg cct ttg; i.e., SEQ ID NO: 6), or SEQ ID NO: 1 (e.g., SEQ ID NO: 3 above). The invention also features an isolated nucleic acid containing a sequence at least 70% (e.g., 90%, 95%, or 100%, or any other number between 70% and 100%, inclusive) identical to SEQ ID NO: 3.

The percent identity of two amino acid sequences is determined using the algorithm of Karlin and Altschul ((1990) Proc. Natl. Acad. Sci. USA 87, 2264-2268), modified as in Karlin and Altschul ((1993) Proc. Natl. Acad. Sci. USA 90, 5873-5877). Such an algorithm is incorporated into the XBLAST programs of Altschul, et al. ((1990) J. Mol. Biol. 215, 403-410). BLAST protein searches are performed with the XBLAST program, score=50, wordlength=3. Where gaps exist between two sequences, Gapped BLAST is utilized as described in Altschul, et al. ((1997) Nucleic Acids Res. 25, 3389-3402). When employing BLAST and Gapped BLAST programs, one can conveniently use the default parameters (e.g., XBLAST). See ncbi.nlm.nih.gov.

A nucleic acid refers to a DNA molecule (e.g., a cDNA or genomic DNA), an RNA molecule (e.g., an mRNA), or a DNA or RNA analog. A DNA or RNA analog can be synthesized from nucleotide analogs. The nucleic acid molecule can be single-stranded or double-stranded, but preferably is double-stranded DNA. An "isolated nucleic acid" refers to a nucleic acid the structure of which is not identical to that of any naturally occurring nucleic acid or to that of any fragment of a naturally occurring genomic nucleic acid. The term therefore covers, for example, (a) a DNA which has the sequence of part of a naturally occurring genomic DNA molecule but is not flanked by both of the coding sequences that flank that part of the molecule in the genome of the organism in which it naturally occurs; (b) a nucleic acid incorporated into a vector or into the genomic DNA of a prokaryote or eukaryote in a manner such that the resulting molecule is not identical to any naturally occurring vector or genomic DNA; (c) a separate molecule such as a cDNA, a genomic fragment, a fragment produced by polymerase chain reaction (PCR), or a restriction fragment; and (d) a recombinant nucleotide sequence that is part of a hybrid gene, i.e., a gene encoding a fusion protein. The nucleic acid described above can be used to express the polypeptide of this invention. For this purpose, one can operatively linked the nucleic acid to suitable regulatory sequences to generate an expression vector.

A vector refers to a nucleic acid molecule capable of transporting another nucleic acid to which it has been linked. The vector can be capable of autonomous replication or integrate into a host DNA. Examples of the vector include a plasmid, cosmid, or viral vector. The vector of this invention includes a nucleic acid in a form suitable for expression of the nucleic acid in a host cell. Preferably the vector includes one or more regulatory sequences operatively linked to the nucleic acid sequence to be expressed. A "regulatory sequence" includes promoters, enhancers, and other expression control elements (e.g., polyadenylation signals). Regulatory sequences include those that direct constitutive expression of a nucleotide sequence, as well as tissue-specific regulatory and/or inducible sequences. The design of the expression vector can depend on such factors as the choice of the host cell to be transformed, the level of expression of protein desired, and the like. The expression vector can be introduced into host cells to produce the polypeptide of this invention. Also within the scope of this invention is a host cell that contains the above-described nucleic acid. Examples include *E. coli* cells, insect cells (e.g., using baculovirus expression vectors), yeast cells, or mammalian cells. See e.g., Goeddel, (1990) Gene Expression Technology: Methods in Enzymology 185, Academic Press, San Diego, Calif. To produce a polypeptide of this invention, one can culture a host cell in a medium under conditions permitting expression of the polypeptide encoded by a nucleic acid of this invention, and purify the polypeptide from the cultured cell or the medium of the cell. Alternatively, the nucleic acid of this invention can be transcribed and translated in vitro, for example, using T7 promoter regulatory sequences and T7 polymerase.

A polypeptide and a nucleic acid of this invention can be used to induce an immune response (i.e., the production of specific antibodies) in a subject against a coronavirus by administering to the subject an effective amount of the polypeptide or nucleic acid encoding the polypeptide. They also can be used to generate specific antibodies that bind specifically to a polypeptide having the sequence of SEQ ID NO: 1, 2 or 5, or its immunogenic fragment. More specifically, one can generate the antibodies by administering to a non-human animal the polypeptide or nucleic acid. Thus, within the scope of this invention is an immunogenic composition containing the afore-mentioned polypeptide or nucleic acid; and a pharmaceutically acceptable carrier. The composition can be used to generate the antibodies. One can purify the antibodies from the subject or the non-human animal and generate monoclonal antibodies by standard techniques.

One can use the just-described antibodies to diagnose an infection with a coronavirus, e.g., SARS-CoV, in a subject by determining the presence of a polypeptide containing the sequence of SEQ ID NO: 1 or an immunogenic fragment thereof (e.g., SEQ ID NO: 2 or 5) in a test sample from the subject. Presence of the polypeptide in the test sample indicates the subject is infected with the coronavirus. One can also diagnose an infection with a coronavirus in a subject by determining presence of a specific antibody against a polypeptide having the sequence of SEQ ID NO: 1 or an immunogenic fragment thereof in the test sample. Presence of the antibody in the test sample also indicates the subject is infected with the coronavirus.

A polypeptide of this invention can be used in a screening method of identifying a compound for treating an infection with a coronavirus, e.g., SARS virus. The method includes (1) contacting a test compound with the above-described polypeptide; and (2) determining a binding between the test compound and the polypeptide. A presence of the binding indicates that the test compound can be used to treat an infection with the coronavirus.

Also within the scope of this invention is a method of treating an infection with a coronavirus. The method includes administering to a subject in need thereof an effective amount of one or more of the above-described polypeptides or antibodies. The term "treating" is defined as administration of a composition to a subject with the purpose to cure, alleviate, relieve, remedy, prevent, or ameliorate a disorder, the symptom of the disorder, the disease state secondary to the disorder, or the predisposition toward the disorder. An "effective amount" is an amount of the composition that is capable of producing a medically desirable result, e.g., as described above, in a treated subject.

The details of one or more embodiments of the invention are set forth in the description below. Other features, objects, and advantages of the invention will be apparent from the description and from the claims.

DETAILED DESCRIPTION

The present invention relates to the protein 3a of the SARS virus and its fragments. These polypeptides can be targeted for diagnosing or treating SARS.

The genome of SARS-CoV, 29.7 kb in length, has a typical genomic organization of coronaviruses, which have the characteristic gene order [5'-replicase (rep), spike(S), envelope (E), membrane (M) and nucleocapsid (N)-3'] and short untranslated regions at both termini. (Rota et al., 2003, Science, 300, 1394-1399). The SARS-CoV genome contains fourteen putative open reading frames (ORFs), which encodes six known and eight unknown proteins (Snijder et al., 2003, J. Mol. Bio. 331, 991-1004; and Thiel et al., 2003, J. Gen. Virol., 84, 2305-2315). The ORF 3a of SARS-CoV genome, located between genes encoding the S and E protein, encodes an unknown function protein 3a.

As shown in the examples below, protein 3a indeed is expressed by SARS-CoV. A polypeptide of this invention contains SEQ ID NO: 1 or an immunogenic fragment thereof. Also within the scope of this invention are functional equivalents of SEQ ID NO: 1. A functional equivalent of SEQ ID NO: 1 refers to a polypeptide derived from the coronavirus protein 3a, e.g., a fusion polypeptide or a polypeptide having one or more point mutations, insertions, deletions, truncations, or a combination thereof. In particular, such functional equivalents include polypeptides, whose sequences differ from protein 3a by one or more conservative amino acid substitutions or by one or more non-conservative amino acid substitutions, deletions, or insertions. Such a functional equivalent can be encoded by a nucleic acid that hybridizes under high stringency conditions to a probe the sequence of which consists of SEQ ID NO: 3, 4, or 6. The term "hybridizes under stringent conditions" refers to conditions for hybridization in 6× sodium chloride/sodium citrate (SSC) at about 45° C., followed by one or more washes in 0.2×SSC, 0.1% SDS at 50-65° C. All of the above-described functional equivalents retain substantially the sub-cellular targeting activity of protein 3a, i.e., the ability of directing polypeptides to a particular sub-cellular compartment as described in Example 5 below. This activity can be determined by the immuno-fluorescence microscopy or cell-fractionation assay described in the example.

The protein 3a polypeptide or its immunogenic fragments can be obtained as a synthetic polypeptide or a recombinant polypeptide. To prepare a recombinant polypeptide, a nucleic acid encoding it can be linked to another nucleic acid encoding a fusion partner, e.g., Glutathione-S-Transferase (GST), 6×-His epitope tag, or M13 Gene 3 protein. The resultant fusion nucleic acid expresses in suitable host cells a fusion protein that can be isolated by methods known in the art. The isolated fusion protein can be further treated, e.g., by enzymatic digestion, to remove the fusion partner and obtain the recombinant polypeptide of this invention.

A polypeptide of the invention can be used to generate antibodies in animals (for production of antibodies) or humans (for treatment of diseases). Methods of making monoclonal and polyclonal antibodies and fragments thereof in animals are known in the art. See, for example, Harlow and Lane, (1988) Antibodies: A Laboratory Manual, Cold Spring Harbor Laboratory, New York. The term "antibody" includes intact molecules as well as fragments thereof, such as Fab, F(ab')$_2$, Fv, scFv (single chain antibody), and dAb (domain antibody; Ward, et. al. (1989) Nature, 341, 544). These antibodies can be used for detecting protein 3a, e.g., in determining whether a test sample from a subject contains SARS virus or in identifying a compound that binds to the polypeptide. These antibodies are also useful for treating SARS.

In general, a polypeptide of the invention can be coupled to a carrier protein, such as KLH, mixed with an adjuvant, and injected into a host animal. Antibodies produced in that animal can then be purified by peptide affinity chromatography. Commonly employed host animals include rabbits, mice, guinea pigs, and rats. Various adjuvants that can be used to increase the immunological response depend on the host species and include Freund's adjuvant (complete and incomplete), mineral gels such as aluminum hydroxide, surface active substances such as lysolecithin, pluronic polyols, polyanions, peptides, oil emulsions, keyhole limpet hemocyanin, and dinitrophenol. Useful human adjuvants include BCG (bacille Calmette-Guerin) and *Corynebacterium parvum*.

Polyclonal antibodies, heterogeneous populations of antibody molecules, are present in the sera of the immunized subjects. Monoclonal antibodies, homogeneous populations of antibodies to a polypeptide of this invention, can be prepared using standard hybridoma technology (see, for example, Kohler et al. (1975) Nature 256, 495; Kohler et al. (1976) Eur. J. Immunol. 6, 511; Kohler et al. (1976) Eur. J. Immunol. 6, 292; and Hammerling et al. (1981) Monoclonal Antibodies and T Cell Hybridomas, Elsevier, N.Y.). In particular, monoclonal antibodies can be obtained by any technique that provides for the production of antibody molecules by continuous cell lines in culture such as described in Kohler et al. (1975) Nature 256, 495 and U.S. Pat. No. 4,376,110; the human B-cell hybridoma technique (Kosbor et al. (1983) Immunol Today 4, 72; Cole et al. (1983) Proc. Natl. Acad. Sci. USA 80, 2026, and the EBV-hybridoma technique (Cole et al. (1983) Monoclonal Antibodies and Cancer Therapy, Alan R. Liss, Inc., pp. 77-96). Such antibodies can be of any immunoglobulin class including IgG, IgM, IgE, IgA, IgD, and any subclass thereof. The hybridoma producing the monoclonal antibodies of the invention may be cultivated in vitro or in vivo. The ability to produce high titers of monoclonal antibodies in vivo makes it a particularly useful method of production.

In addition, techniques developed for the production of "chimeric antibodies" can be used. See, e.g., Morrison et al. (1984) Proc. Natl. Acad. Sci. USA 81, 6851; Neuberger et al. (1984) Nature 312, 604; and Takeda et al. (1984) Nature 314:452. A chimeric antibody is a molecule in which different portions are derived from different animal species, such as those having a variable region derived from a murine monoclonal antibody and a human immunoglobulin constant region. Alternatively, techniques described for the production of single chain antibodies (U.S. Pat. Nos. 4,946,778 and 4,704,692) can be adapted to produce a phage library of single chain Fv antibodies. Single chain antibodies are formed by linking the heavy and light chain fragments of the Fv region via an amino acid bridge. Moreover, antibody fragments can be generated by known techniques. For example, such fragments include, but are not limited to, F(ab')$_2$ fragments that can be produced by pepsin digestion of an antibody molecule, and Fab fragments that can be generated by reducing the disulfide bridges of F(ab')$_2$ fragments. Antibodies can also be humanized by methods known in the art. For example, monoclonal antibodies with a desired binding specificity can be commercially humanized (Scotgene, Scotland; and Oxford Molecular, Palo Alto, Calif.). Fully human antibodies, such as those expressed in transgenic animals are also features of the invention (see, e.g., Green et al. (1994) Nature Genetics 7, 13; and U.S. Pat. Nos. 5,545,806 and 5,569,825).

A polypeptide of the invention can also be used to prepare an immunogenic composition (e.g., a vaccine) for generating antibodies against coronavirus (e.g., SARS CoV) in a subject susceptible to the coronavirus. Such compositions can be prepared, e.g., according to the method described in the examples below, or by any other equivalent methods known in the art. The composition contains an effective amount of a polypeptide of the invention, and a pharmaceutically acceptable carrier such as phosphate buffered saline or a bicarbonate solution. The carrier is selected on the basis of the mode and route of administration, and standard pharmaceutical practice. Suitable pharmaceutical carriers and diluents, as well as pharmaceutical necessities for their use, are described in Remington's Pharmaceutical Sciences. An adjuvant, e.g., a cholera toxin, *Escherichia coli* heat-labile enterotoxin (LT), liposome, immune-stimulating complex (ISCOM), or immunostimulatory sequences oligodeoxynucleotides (ISS-ODN), can also be included in a composition of the invention, if necessary. Protein 3a, fragments or analogs thereof may be components of a multivalent composition of vaccine against respiratory diseases. This multivalent composition contains at least one immunogenic fragment of protein 3a described above, along with at least one protective antigen isolated from influenza virus, para-influenza virus 3, *Strentococcus pneumoniae, Branhamella* (*Moroxella*) *gatarhalis, Staphylococcus aureus*, or respiratory syncytial virus, in the presence or absence of adjuvant.

Methods for preparing vaccines are generally well known in the art, as exemplified by U.S. Pat. Nos. 4,601,903; 4,599,231; 4,599,230; and 4,596,792. Vaccines may be prepared as injectables, as liquid solutions or emulsions. Protein 3a, fragments or analogs thereof may be mixed with physiologically acceptable and excipients compatible. Excipients may include, water, saline, dextrose, glycerol, ethanol, and combinations thereof. The vaccine may further contain minor amounts of auxiliary substances such as wetting or emulsifying agents, pH buffering agents, or adjuvants to enhance the effectiveness of the vaccines. Methods of achieving adjuvant effect for the vaccine include use of agents, such as aluminum hydroxide or phosphate (alum), commonly used as 0.05 to 0.1 percent solutions in phosphate buffered saline. Vaccines may be administered parenterally, by injection subcutaneously or intramuscularly. Alternatively, other modes of administration including suppositories and oral formulations may be desirable. For suppositories, binders and carriers may include, for example, polyalkalene glycols or triglycerides. Oral formulations may include normally employed incipients such as, for example, pharmaceutical grades of saccharine, cellulose, magnesium carbonate and the like. These compositions take the form of solutions, suspensions, tablets, pills, capsules, sustained release formulations or powders and contain 10-95% of protein 3a, fragment analogs, or peptides.

The vaccines are administered in a manner compatible with the dosage formulation, and in an amount that is therapeutically effective, protective and immunogenic. The quantity to be administered depends on the subject to be treated, including, for example, the capacity of the individual's immune system to synthesize antibodies, and if needed, to produce a cell-mediated immune response. Precise amounts of active ingredient required to be administered depend on the judgment of the practitioner. However, suitable dosage ranges are readily determinable by one skilled in the art and may be of the order of micrograms of the polypeptide of this invention. Suitable regimes for initial administration and booster doses are also variable, but may include an initial administration followed by subsequent administrations. The dosage of the vaccine may also depend on the route of administration and varies according to the size of the host.

Use of polypeptide in vivo may first require chemical modification of the peptides since they may not have a sufficiently long half-life. A chemically modified peptide or a peptide analog includes any functional chemical equivalent of the peptide characterized by its increased stability and/or efficacy in vivo or in vitro in respect of the practice of the invention. The term peptide analog also refers to any amino acid derivative of a peptide as described herein. A peptide analog can be produced by procedures that include, but are not limited to, modifications to side chains, incorporation of unnatural amino acids and/or their derivatives during peptide synthesis and the use of cross-linkers and other methods that impose conformational constraint on the peptides or their analogs. Examples of side chain modifications include modification of amino groups, such as by reductive alkylation by reaction with an aldehyde followed by reduction with NaBH$_4$; amidation with methylacetimidate; acetylation with acetic anhydride; carbamylation of amino groups with cyanate; trinitrobenzylation of amino groups with 2, 4, 6, trinitrobenzene sulfonic acid (TNBS); alkylation of amino groups with succinic anhydride and tetrahydrophthalic anhydride; and pyridoxylation of lysine with pyridoxa-5'-phosphate followed by reduction with NABH$_4$. The guanidino group of arginine residues may be modified by the formation of heterocyclic condensation products with reagents such as 2,3-butanedione, phenylglyoxal and glyoxal. The carboxyl group may be modified by carbodiimide activation via o-acylisourea formation followed by subsequent derivatization, for example, to a corresponding amide. Sulfhydryl groups may be modified by methods, such as carboxymethylation with iodoacetic acid or iodoacetamide; performic acid oxidation to cysteic acid; formation of mixed disulphides with other thiol compounds; reaction with maleimide; maleic anhydride or other substituted maleimide; formation of mercurial derivatives using 4-chloromercuribenzoate, 4-chloromercuriphenylsulfonic acid, phenylmercury chloride, 2-chloromercuric-4-nitrophenol and other mercurials; carbamylation with cyanate at alkaline pH. Tryptophan residues may be modified by, for example, oxidation with N-bromosuccinimide or alkylation of the indole ring with 2-hydroxy-5-nitrobenzyl bromide or sulphonyl halides. Tryosine residues may be altered by nitration with tetranitromethane to form a 3-nitrotyrosine derivative. Modification of the imidazole ring of a histidine residue may be accomplished by alkylation with iodoacetic acid derivatives or N-carbethoxylation with diethylpyrocarbonate. Examples of incorporating unnatural amino acids and derivatives during peptide synthesis include, but are not limited to, use of norleucine, 4-amino butyric acid, 4-amino-3-hydroxy-5-phenylpentanoic acid, 6-aminohexanoic acid, t-butylglycine, norvaline, phenylglycine, ornithine, sarcosine, 4-amino-3-hydroxy-6-methylheptanoic acid, 2-thienyl alanine and/or D-isomers of amino acids.

A nucleic acid molecule of this invention may also be used directly for immunization by administration of the nucleic acid directly to a subject via a live vector, such as *Salmonella*, BCG, adenovirus, poxvirus or vaccinia. Immunization methods based on nucleic acids are well known in the art.

A subject susceptible to coronavirus infection can be identified and administered a polypeptide-containing composition of the invention. The dose of the composition depends, for example, on the particular polypeptide, whether an adjuvant is co-administered with the polypeptide, the type of adjuvant co-administered, the mode and frequency of administration, as can be determined by one skilled in the art. Administration is repeated as necessary, as can be determined by one skilled in the art. For example, a priming dose can be followed by three booster doses at weekly intervals. A booster shot can be given at 4 to 8 weeks after the first immunization, and a second booster can be given at 8 to 12 weeks, using the same formulation. Sera or T-cells can be taken from the subject for testing the immune response elicited by the composition against the coronavirus protein 3a or infection. Methods of assaying antibodies or cytotoxic T cells against a protein or infection are well known in the art. Additional boosters can be given as needed. By varying the amount of polypeptide, the dose of the composition, and frequency of administration, the immunization protocol can be optimized for eliciting a maximal immune response. Before a large scale administering, efficacy testing is desirable. In an efficacy testing, a non-human subject can be administered via an oral or parenteral route with a composition of the invention. After the initial administration or after optional booster administration, both the test subject and the control subject (receiving mock administration) are challenged with an $LD_{95}$ dose of a coronavirus. End points other than lethality can also be used. Efficacy is determined if subjects receiving the composition dies at a rate lower than control subjects. The difference in death rates should be statistically significant.

Also within the scope of this invention is a diagnosing method using the above-described antibodies or protein 3a fragments. Presence of antibodies against a protein 3a fragment or the polypeptide itself in a subject indicates that the subject is infected with a coronavirus. To detect the antibodies or polypeptide, one can obtain a test sample from a subject and detect the presence or absence of the antibodies or polypeptide using standard techniques. Examples of the techniques include ELISAs, immunoprecipitations, immunofluorescence, EIA, RIA, and Western blotting analysis. The sample can be a clinical sample, including exudates, body fluids (e.g., serum, amniotic fluid, middle ear effusion, sputum, bronchoalveolar lavage fluid) and tissues.

The nucleic acid of this invention is useful as a hybridization probe for identifying coronavirus, e.g., SARS CoV, in a sample. A variety of hybridization conditions may be employed to achieve varying degrees of selectivity of the probe toward the target sequences. A high degree of selectivity requires stringent conditions, such as that described in the Summary section A hybridization reaction can be performed both in a solution or on a solid phrase. In a solid phase, a test sequence from a sample is affixed to a selected matrix or surface. The fixed nucleic acid is then subjected to specific hybridization with selected probes comprising the nucleic acid of the present invention under desired conditions. The selected conditions will depend on the particular circumstances based on the particular criteria required depending on, for example, on the G+C contents, type of target nucleic acid, source of nucleic acid, size of hybridization probe etc. Following washing of the hybridization surface to remove non-specifically bound probe molecules, specific hybridization is detected or quantified, by means of the label. The selected probe should be at least 18 bp and may be in the range of 30 bp to 90 bp long.

Within the scope of the invention is a novel compound (e.g., an antibody) that binds to a polypeptide of the invention. Such a compound can be designed, e.g., using computer modeling programs, according to the three-dimensional conformation of the polypeptide, and synthesized using methods known in the art. It can also be identified by library screening. To screen for such a compound, one can (1) contact a candidate compound and a protein 3a fragment and (2) determine a binding between the test compound and the polypeptide. A presence of the binding indicates that the test compound can be used to treat an infection with the coronavirus.

Test compounds can be obtained using any of the numerous approaches in combinatorial library methods known in the art. Such libraries include: peptide libraries, peptoid libraries (libraries of molecules having the functionalities of peptides, but with a novel, non-peptide backbone that is resistant to enzymatic degradation), spatially addressable parallel solid phase or solution phase libraries, synthetic libraries obtained by deconvolution or affinity chromatography selection, the "one-bead one-compound" libraries, and antibody libraries. See, e.g., Zuckermann et al. (1994) J. Med. Chem. 37, 2678-85; Lam (1997) Anticancer Drug Des. 12, 145; Lam et al. (1991) Nature 354, 82; Houghten et al. (1991) Nature 354, 84; and Songyang et al. (1993) Cell 72, 767. Examples of methods for the synthesis of molecular libraries can be found in the art, for example, in: DeWitt et al. (1993) Proc. Natl. Acad. Sci. USA 90, 6909; Erb et al. (1994) Proc. Natl. Acad. Sci. USA 91, 11422; Zuckermann et al. (1994) J. Med. Chem. 37, 2678; Cho et al. (1993) Science 261, 1303; Carrell et al. (1994) Angew. Chem. Int. Ed. Engl. 33, 2059; Carell et al. (1994) Angew. Chem. Int. Ed. Engl. 33, 2061; and Gallop et al. (1994) J. Med. Chem. 37,1233. Libraries of compounds may be presented in solution (e.g., Houghten (1992) Biotechniques 13, 412-421), or on beads (Lam (1991) Nature 354, 82-84), chips (Fodor (1993) Nature 364, 555-556), bacteria (U.S. Pat. No. 5,223,409), spores (U.S. Pat. No. 5,223,409), plasmids (Cull et al. (1992) Proc. Natl. Acad. Sci. USA 89, 1865-1869), or phages (Scott and Smith (1990) Science 249, 386-390; Devlin (1990) Science 249, 404-406; Cwirla et al. (1990) Proc. Natl. Acad. Sci. USA 87, 6378-6382; Felici (1991) J. Mol. Biol. 222, 301-310; and U.S. Pat. No. 5,223, 409).

The above-described antibodies and compounds can be used for treating SARS. The invention therefore features a method of treating SARS, e.g., by administering to a subject in need thereof an effective amount of an antibody or compound of the invention. Subjects to be treated can be identified as having, or being at risk for acquiring, a condition characterized by SARS. This method can be performed alone or in conjunction with other drugs or therapy.

In one in vivo approach, a therapeutic composition (e.g., a composition containing a polypeptide, an antibody, or a compound of the invention) is administered to a subject. Generally, the antibody or the compound is suspended in a pharmaceutically-acceptable carrier (e.g., physiological saline) and administered orally or by intravenous infusion, or injected or implanted subcutaneously, intramuscularly, intrathecally, intraperitoneally, intrarectally, intravaginally, intranasally, intragastrically, intratracheally, or intrapulmonarily.

The dosage required depends on the choice of the route of administration; the nature of the formulation; the nature of the subject's illness; the subject's size, weight, surface area, age, and sex; other drugs being administered; and the judgment of the attending physician. Suitable dosages are in the range of 0.01-100.0 mg/kg. Wide variations in the needed dosage are to be expected in view of the variety of compositions available and the different efficiencies of various routes of administration. For example, oral administration would be expected to require higher dosages than administration by intravenous injection. Variations in these dosage levels can be adjusted using standard empirical routines for optimization as is well understood in the art. Encapsulation of the composition in a suitable delivery vehicle (e.g., polymeric microparticles or implantable devices) may increase the efficiency of delivery, particularly for oral delivery.

Also within the scope of this invention is a pharmaceutical composition that contains a pharmaceutically acceptable carrier and an effective amount of an antibody or a compound of the invention. The pharmaceutical composition can be used to treat SARS. The pharmaceutically acceptable carrier includes a solvent, a dispersion medium, a coating, an antibacterial and antifungal agent, and an isotonic and absorption delaying agent.

A pharmaceutical composition of the invention can be formulated into dosage forms for different administration routes utilizing conventional methods. For example, it can be formulated in a capsule, a gel seal, or a tablet for oral administration. Capsules can contain any standard pharmaceutically acceptable materials such as gelatin or cellulose. Tablets can be formulated in accordance with conventional procedures by compressing mixtures of the composition with a solid carrier and a lubricant. Examples of solid carriers include starch and sugar bentonite. The composition can also be administered in a form of a hard shell tablet or a capsule containing a binder, e.g., lactose or mannitol, a conventional filler, and a tableting agent.

The pharmaceutical composition can be administered via the parenteral route. Examples of parenteral dosage forms include aqueous solutions, isotonic saline or 5% glucose of the active agent, or other well-known pharmaceutically acceptable excipient. Cyclodextrins, or other solubilizing agents well known to those familiar with the art, can be utilized as pharmaceutical excipients for delivery of the therapeutic agent.

The efficacy of a composition of this invention can be evaluated both in vitro and in vivo. For in vivo studies, the composition can be injected into an animal (e.g., a mouse model) and its therapeutic effects are then accessed. Based on the results, an appropriate dosage range and administration route can be determined The specific examples below are to be construed as merely illustrative, and not limitative of the remainder of the disclosure in any way whatsoever. Without further elaboration, it is believed that one skilled in the art can, based on the description herein, utilize the present invention to its fullest extent. All publications cited herein are hereby incorporated by reference in their entirety.

THE EXAMPLES

Example 1

Total RNA was isolated from Vero E6 cells infected by SARS-CoV (TW1 strain) via a single-step extraction method as described in Hsueh et al., 2003, Emerg. Infect. Dis. 9, 1163-1167 or Chomczynski et al., 1987, Anal. Biochem. 162, 156-159. Primers used for amplifying and sequencing the gene encoding the putative protein 3a (open reading frame 3a, ORF 3a) were designed based on nucleotides 25268-26092 of the GenBank accession number: AY291451. This putative gene (Marra et al., Science. 2003 May 30; 300:1399-404) is located between the S glycoprotein gene (CDS: 21492~25259) and the E protein gene (CDS: 26117~26347). A minimal transcription regulatory sequence (5'-ACGAAC-3') is located upstream of ORF 3a (CDS: 25260~25265). The following two oligonucleotides were used:

```
sense primer:
5'-ATGGATTTGTTTATGAGATTTTTTACT-3'   (SEQ ID NO: 9)

antisense primer
5'-CAAAGGCACGCTAGTAGTCGTCGT-3'      (SEQ ID NO: 10)
```

These two primers correspond to the N-terminal MDLFMR-FFT (SEQ ID NO: 11) segment and the C-terminus TTTTS-VPL (SEQ ID NO: 12) segment, respectively. The open reading frame was then amplified by PCR. The amplified products were analyzed by electrophoresis, subcloned into the pST-Blue vector (Novagen, Madison, Wis.), and then transformed into E. coli strain DH5a. Plasmids from positive clones were subjected to sequence analysis by an ABI 3100 sequencer (Applied Biosystems, Foster City, Calif.).

It was predicted that the open reading frame encoded a 274-amino acid protein (i.e., protein 3a) having a theoretical molecular mass of approximately 30.9 kDa. By BLAST analysis, it was shown that the N-terminal part of protein 3a shared ~29% identity with the putative cytochrome B-561 transmembrane protein from bacteria (*Ralstonia solanacearum*), and 24% identity with the opsin fragments from the hawkmoth (*Manduca sexta*) and the rhodopsin from the butterfly (*Popilio glaucus*). The C terminus part had moderate similarity (41% and 27%, respectively) to the calcium-transporting ATPase of a parasite (*Plasmodium falciparum*) and the outer-membrane porin of a bacterium (*Shewanella oneidensis*). The full-length protein 3a sequence lacked significant similarity to any known proteins.

Hydrophobicity and polarity of protein 3a were examined by standard techniques (Hopp et al., 1981, Proc. Natl. Acad. Sci. USA. 78, 3824-3828 and Grantham, 1974, Science 185, 862-864). Three regions of low polarity and high hydrophobicity were found in the N terminus section. Membrane spanning regions, predicted by the Dense Alignment Surface method (Cserzo et al., 1997, Prot. Eng. 10, 673-676), were located in the following three regions: amino acids 43-56, 79-97, and 106-116. These results indicate that protein 3a plays a role in SARS-CoV interaction with the cellular membrane.

Example 2

Recombinant protein 3a was generated. The above-described coding sequence was inserted into the vector pGEX 4T-2 (Amersham Biosciences Inc., Sweden) and in-frame fused to the sequence encoding glutathione S-transferase (GST). The resulting vector was transformed into E. coli strain BL21 (DE3) (Novagen, Madison, Wis.). The GST-protein 3a fusion was induced to express by 0.5 mM isopropyl-β-D-thiogalasctopyranoside for 3 hour at 37° C. To obtain pure recombinant protein 3a, the GST tag was removed by thrombin protease digestion and then by glutathione-Sepharose 4B affinity chromatography (Amersham Biosciences Inc.) according to the manufacturer's instructions. Briefly, the induced BL21 cells were suspended in a PBS buffer containing 1 mM PMSF and then sonicated in an ice bath for 1 minute. The lysed cells were centrifuged at 20,000×g at 4° C. for 15 minutes. The supernatant was applied to a glutathione-Sepharose 4B column equilibrated with a PBS buffer, and the column was then washed with 10 times the bed volume of the same PBS buffer. After the GST-protein 3a fusion was bound, the column was incubated with PBS containing 50 units of thrombin at 25° C. for 2 hours. GST-free recombinant protein 3a was eluted with PBS and collected. The protein purity was determined by 12.5% SDS-PAGE electrophoresis and visualized by Coomassie blue.

Example 3

Polyclonal antibodies against protein 3a were generated. Standard techniques were used to synthesize two peptides CPIYDEPTTTTSVPL (peptide P2, SEQ ID NO:7) and SDNGPQSNQRSAC (peptide N1, SEQ ID NO: 8), which contain residues 261-274 of protein 3a (i.e., SEQ ID NO: 5) and residues 1-12 of the nucleocapsid protein, respectively. Each of the two peptides was conjugated to keyhole limpet hemocyanin, dissolved in 0.5 ml of PBS, and emulsified with an equal volume of the Titer Max adjuvant (CytRx Inc., Norcross, Ga.), before being administered to 3-month-old New Zealand white rabbits. Three weeks later, the rabbits were boosted by each of the two conjugated-peptides emulsified in Freund's incomplete adjuvant via intradermal injection. They were boosted again in the same manner after another 3 weeks. Antisera were then collected at 12-day intervals starting from the last boosting. The antibody specificity was examined by Western blotting.

More specifically, protein samples were separated on a 12.5%-SDS/PAGE gel before being electro-blotted onto a PVDF membrane. The membrane was then blocked in skim milk and incubated for 16 hour at 4° C. with anti-P2 rabbit antiserum (diluted 1: 2000~3000) or a pooled sera from SARS-CoV-infected patients (diluted 1:100). Bound antibodies were detected by horseradish peroxidaselabeled donkey anti-rabbit IgG antibodies (Amersham Biosciences Inc.) or sheep anti-human IgG antibodies (Amersham Biosciences Inc.). The target proteins were visualized by an enhanced chemiluminescence (ECL, Amersham Biosciences Inc.) development system.

The results showed that purified recombinant protein 3a from *E. coli* was recognized by anti-P2 antibody and pooled sera from SARS-CoV-infected patients. By contrast, this protein was not detected by a pre-immune serum, indicating that SARS-CoV indeed expresses protein 3a.

Example 4

Recombinant protein 3a was transiently expressed in Vero E6 cells. More specifically, the above-described sequence encoding protein 3a was subcloned into the pcDNA 3.1/Myc-His vector (Invitrogen, San Diego, Calif.). Vero E6 cells (ATCC CRL-1586) were cultured in a Dulbecco's Modified Eagle's Medium (DMEM, Gibco-BRL) supplemented with 2 mM L-glutamine, 1% penicillin/streptomycin, and 10% fetal bovine serum (FBS).

The pcDNA3.1/Myc-His/protein 3a plasmid was mixed with a Lipofectin reagent (Invitrogen, San Diego, Calif.) and transfected into the cells according to the manufacturer's instructions. After 48 hours, the cells were harvested, washed twice with PBS, and subjected to Western blotting. It was found that no protein 3a expression was detected. Attempts were made to express SARS protein 3a in several other cell lines, but all were unsuccessful.

It was hypothesized that protein 3a might only selectively express in SARS-CoV infected cells. Accordingly, an infected-transfection transient expression system was used to express protein 3a in Vero E6 cells (Chomczynski et al., 1987, Anal. Biochem. 162, 156-159; Wyatt et al., 1995, Virology 210, 202-205; Fuerst et al., 1986, Proc. Natl. Acad. Sci. USA. 83, 8122-8126; and Lewis et al., 1996, J. Virol. 70, 2869-2875). Vero E6 cells ($1\times10^6$) was first infected with $1\times10^5$ infectious units of vaccinia virus/bacteriophage T7 RNA polymerase hybrid. Two hours later, they were transfected with aproximately 15 µg of DNA, harvested, and subjected to Western blotting analysis using anti-P2 antibody in the manner described above. It was found that the cells expressed the recombinant Myc-His tagged protein 3a, which had the expected molecular mass of ~37 kDa. No signal was detected in lysates from non-infected-transfected cells.

To further confirm that SARS-CoV expresses protein 3a, Vero E6 cells were infected with SARS-CoV TW1 for 4, 8, 12, or 24 hours. The infected cells, as well as control non-infected cells, were harvested and treated with a SDS-sample buffer to generate cell lysates. The lysates were examined by SDS-PAGE/Coomassie blue staining or Western blotting using anti-P2 antibody, anti-P2 antibody pre-incubated with 5 mM of P2 peptide, or anti-nucleocapsid (anti-N1) antibody, in the manner described above.

It was found that expression of protein 3a, like that of nucleocapsid protein, was detected at 8-12 hours after infection and reached a higher level after ~24 hours. Pre-incubation of anti-P2 antibody with P2 peptides, but not N1 peptides, prevented binding of anti-P2 antibodies to protein 3a, indicating that protein 3a was specifically detected.

Example 5

Sub-cellular localization of protein 3a was examined by both immuno-fluorescence microscopy and cell fractionation.

For immunofluorescence microscopy, $6\times10^4$ Vero E6 cells were grown on cover slips in a 12-well plate and then infected-transfected with 1 µg pcDNA3.1/Myc-His protein 3a plasmid in the manner describe above. Forty-eight hours later, the cells were washed with PBS twice, fixated in 4% paraformaldehyde-PBS for 5 minutes at room temperature, and permeabilized in ice-cold methanol for 5 minutes. Indirect immunofluorescence staining was performed by a standard method (Lin et al., 2000, J. Biol. Chem. 275, 37815-37823). The cells were blocked with 0.2% bovine serum albumin, 0.1% saponin in PBS, followed by incubation with anti-P2 peptide-specific rabbit antiserum (1:600) or anti-SARS M protein rabbit antiserum for 30 minutes. To visualize cell organelles, a number of organelle-specific antibodies (diluted 1:1000) were respectively co-incubated with anti-P2 antibody. These antibodies included mouse monoclonal antibodies to Golgi 58K protein (Sigma), mouse monoclonal antibodies to β-COP protein (Sigma), mouse monoclonal antibodies to calnexin protein (Affinity BioReagents), mouse monoclonal antibodies to lysosomal-associated membrane proteins-2 (LAPM-2) (BD Biosciences), and mouse monoclonal antibodies to cytochrome c oxidase subunit 1 (COX 1) (Molecular Probes).

After three washes with PBS, the cells were incubated with secondary antibodies, including Alexa 488-conjugated anti-rabbit IgG antibody (Molecular Probes), and Alexa 594-conjugated anti-mouse IgG antibody before being stained by DNA dye Hoescht 33258. Finally, the cells were washed three times with PBS again, mounted on Mowiol, and examined under a Zeiss Axiophot microscope equipped for epifluorescence and a Bio-Rad Radiance 2100 confocal microscope.

The results show that, in Vero E6 cells, recombinant protein 3a was distributed over the cytoplasm in a fine punctuate pattern with partly concentrated staining in the Golgi apparatus. Similar immunofluorescence staining of protein 3a was also observed in Vero cells 6 hours after infection of SARS-CoV. However the expression level was lower than that of 24 hours after infection. Furthermore, identical study on a commercially available slide of SARS-CoV-infected cells (Euroimmun Inc., Germany) also showed that (1) protein 3a was detected in a punctuate pattern with partly concentrated staining in the Golgi apparatus, but not in endoplasmic reticulum (ER), lysosome, or mitochondria; and (2) protein 3a, as well as M protein, was co-localized with the beta-COP Golgi apparatus marker protein.

Cell fractionation was conducted to further assess the sub-cellular distribution of recombinant protein 3a in Vero E6 cells. Cytosol (C) and membrane (M) fractions of Vero E6 cells were prepared by CNM compartment protein extraction kit (BioChain Institute Inc., Hayward, Calif.) according to the manufacturer's instructions. Briefly, infected-transfected Vero E 6 cells ($1\times10^6$ cells) were harvested, washed with PBS, and then centrifuged at 1,000×g for 5 minutes. The cell pellet was homogenized in 100 μl of buffer C containing a mixture of protease inhibitors, incubated at 4° C. for 20 minutes, and centrifuged at 4° C., 12,000×g for 20 minutes to generate soluble cytosolic (C) fraction. The insoluble pellet was washed with 200 μl of buffer W and resuspended in 50 μl of buffer N at 4° C. for 20 minutes. The nuclear proteins were extracted and recovered in the supernatant after centrifugation at 4° C., 12,000×g for 20 minutes. Finally, to obtain the membrane proteins, the cell pellet containing cell debris was extracted with 50 μl of buffer M and then incubated at 4° C. for 20 minutes. The supernatant was centrifuged at 4° C., 12,000×g for 20 minutes to generate soluble membrane fraction. All of the fractionated protein solutions were storage at −70° C.

Western blot analysis was used to examine the distribution of protein 3a, calnexin (ER membrane marker), and α-tubulin (cytoplasmic marker) in the sub-cellular fractions. It was found that protein 3a was detected in the membrane fraction. The result demonstrates that the SARS-CoV indeed expresses the membrane-associated protein 3a in vivo. It is known that the viral membrane proteins, including the S protein and M protein, are inserted into the endoplasmic reticulum-Golgi intermediate compartment, whereas full-length replicated RNA (+strands) assembles with the N protein (Fields et al., 2001, Fields Virology Lippincott Williams & Wilkins, Philadelphia, ed. 4.). This RNA-protein complex then associates with the M protein embedded in the membranes of the ER, and virus particles form as the nucleocapsid complex buds into the ER. The virus then migrates through the Golgi complex and eventually exits from the cell, probably by exocytosis. It is of interest to note that protein 3a was partially co-localized with Golgi marker protein p58, and that the punctuate pattern may be the result of protein 3a being a membrane-associated molecule.

Example 6

Expression of protein 3a was examined in a SARS patient, a 73-year-old male admitted to National Taiwan University Hospital due to recurrent chest pain and dyspnea on Apr. 23, 2003. This patient had an episode of myocardial infarction two years earlier. After admission, low-grade fever developed and serial follow-up chest X ray showed progressive lung infiltration. SARS-CoV was isolated from a throat swab and RT-PCR further confirmed presence of the viral genome. At day 7 after admission, the patient died of acute myocardial infarction. Restricted autopsy was performed immediately, and random sampling of the lungs, heart, kidneys, liver, small intestine and spleen were taken. The H-Eosin staining of the lung tissue showed congestion and focal edema. Three lung biopsy specimens without SARS-CoV infection were also included as negative control. All the tissue specimens were fixed in 10% neutral formalin. Paraffin-embedded blocks and serial sections were prepared in a conventional manner.

For immunohistochemical staining, antigen retrieval of the slides was carried out with a steam heat method for 10 minutes using the Trilogy retrieval buffer (Cell Marque Cooperation, Austin, Tex.). The endogenous peroxidase activity was quenched by 0.3% hydrogen peroxide for 20 minute. The slides were incubated with anti-P2 antibody (1:500) or a pre-immune serum at 4° C. overnight. The slides were then sequentially stained on the Nexis autostainer (Ventana, Tucson, Ariz.) using the Ventana Basic Alkaline Phosphatase Red Detection Kit (Ventana) and counterstained with hematoxylin.

It was found that protein 3a was detected only in the lung, but not in the small intestine, heart, liver, spleen, kidney, or lymph node. Positive stains were mostly located in the alveolar lining pneumocytes and in some intra-alveolar cells. The hyaline membrane along the alveolar space was occasionally positive. The positive staining area tended to be found in the periphery of the lung with a patch like distribution. The bronchial epithelium and the endothelium of pulmonary vessels were negative. By contrast, protein 3a was not detected in all tissue sections of non-SARS patients. No staining was seen in the lung tissue sections using the pre-immune serum.

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the scope of the following claims.

What is claimed is:

1. A method of detecting an infection with a coronavirus in a subject, comprising:
   providing a test sample from a subject, and
   determining the presence of a polypeptide in the test sample, wherein the amino acid sequence of the polypeptide is SEQ ID NO: 2 or 5;
   whereby the presence of the polypeptide in the test sample indicates the subject is infected with a coronavirus.

2. The method according to claim 1, wherein the coronavirus is SARS-CoV.

3. The method of claim 1, wherein the amino acid sequence of the polypeptide is SEQ ID NO: 2.

4. The method according to claim 1, wherein the amino acid sequence of the polypeptide is SEQ ID NO: 5.

5. A method of detecting an infection with a coronavirus in a subject, comprising:
   providing a test sample from a subject, and
   determining the presence of an antibody against a polypeptide in the test sample, wherein the amino acid sequence of the polypeptide is SEQ ID NO: 2 or 5;
   whereby the presence of the antibody in the test sample indicates the subject is infected with a coronavirus.

6. The method according to claim 5, wherein the coronavirus is SARS-CoV.

7. The method according to claim 5, wherein the amino acid sequence of the polypeptide is SEQ ID NO: 2.

8. The method according to claim 5, wherein the amino acid sequence of the polypeptide is SEQ ID NO: 5.

* * * * *